United States Patent [19]

Heinonen et al.

[11] Patent Number: 5,772,586
[45] Date of Patent: Jun. 30, 1998

[54] METHOD FOR MONITORING THE HEALTH OF A PATIENT

[75] Inventors: Pekka Heinonen; Harri Okkonen, both of Espoo, Finland

[73] Assignee: Nokia Mobile Phones, Ltd., Finland

[21] Appl. No.: 795,389

[22] Filed: Feb. 4, 1997

[30] Foreign Application Priority Data

Feb. 12, 1996 [FI] Finland .................................. 960636

[51] Int. Cl.$^6$ ....................................................... A61B 5/00
[52] U.S. Cl. ........................... 600/300; 128/904; 600/365
[58] Field of Search .................................... 128/903, 904; 600/309, 365, 301, 300

[56] References Cited

U.S. PATENT DOCUMENTS

| 5,415,167 | 5/1995 | Wilk ...................................... 128/653.1 |
| 5,462,051 | 10/1995 | Oka et al. . |
| 5,507,288 | 4/1996 | Böcker et al. .......................... 128/633 |
| 5,544,661 | 8/1996 | Davis et al. ............................. 128/904 |

FOREIGN PATENT DOCUMENTS

| 0 417 944 B1 | 3/1991 | European Pat. Off. . |
| 0 680 727 A1 | 11/1995 | European Pat. Off. . |
| 7-307803 | 11/1995 | Japan . |
| WO 90/08361 | 7/1990 | WIPO . |

OTHER PUBLICATIONS

"A Telemedicine Distributed Decision–Support System for Diabetes Management", proceedings of the Annual International Conference of the IEEE Engineering in Medicine and Biology Society, vol. 14, Nov. 1992, (Paris, France), pp. 1238–1239, E.J. Goméz et al.

*Primary Examiner*—Jennifer Bahr
*Assistant Examiner*—Eric F. Winaker
*Attorney, Agent, or Firm*—Finnegan, Henderson, Farabow, Garrett, & Dunner, L.L.P.

[57] ABSTRACT

The present invention relates to a method for monitoring the health of a patient by utilizing measurements. In order to improve the contact between the patient and the person treating him, the results of the measurements are supplied via a communications device (1) utilizing a wireless data transmission link to a data processing system (9) available to the person monitoring the patient's health, and the patient's health is monitored by means of the data stored in the data processing system (9).

7 Claims, 1 Drawing Sheet

METHOD FOR MONITORING THE HEALTH OF A PATIENT

FIELD OF THE INVENTION

The present invention relates to a method for monitoring the health of a patient by utilizing measurements. The invention further relates to a system for monitoring the health of a patient, the system comprising a portable measuring device for carrying out a measurement in order to evaluate the patient's health, and a data processing system that is available to a person treating the patient and that maintains data about the results of the performed measurements. The invention also relates to a portable measuring device for carrying out a measurement in order to evaluate the health of a patient.

The invention relates specifically to the self-care and monitoring of the health of a patient with diabetes, but the method, system and measuring device according to the invention can also be utilized in other connections. However, in the following the invention will be described by way of an example specifically in connection with treating diabetes.

DESCRIPTION OF THE PRIOR ART

As is well known, monitoring the health of a patient with diabetes is primarily based on the measurement of the patient's blood glucose level at regular intervals. Treating diabetes requires regular measurements and regular monitoring of the measurement results in order to ensure that the patient's blood glucose level definitely remains within the allowable area and that the patient's medication is optimal.

However, in the present health care system it is not possible for financial and practical reasons for a person specialized in treating diabetes to personally monitor continuously the health of a patient, but the monitoring of the patient's health is largely dependent on the patient himself. Therefore the patient himself must perform measurements at regular intervals. In order to carry out measurements, the patient has to use several instruments which include at present for example a lancet for pricking the skin, a strip for taking a blood sample, and a measuring device to which the strip containing the blood sample is supplied in order to measure the blood glucose level. The prior measuring devices usually measure the blood glucose level either electrically or optically. For the purpose of obtaining data about the development of a patient's health, for example the blood glucose level, over a longer period, the patient must also keep a record of the results of blood samples, for instance.

The fact that a relatively large number of patients with diabetes also contract a secondary disease (e.g. cardiovascular diseases, neuropathy or blindness), which in turn causes considerable costs for the society, clearly indicates that at the moment doctors cannot treat patients with diabetes sufficiently effectively or cannot help the patient to care for himself. One reason for this is that each doctor often treats a high number of patients, whereupon the contact between each individual patient and the doctor is insufficient due to for example too few appointments and the doctor cannot therefore monitor the development of the health of individual patients sufficiently effectively. Also, the data submitted to the doctor is dependent on the patient's own recording, and there is always the possibility that a measurement result is erroneously recorded or it is not recorded at all.

SUMMARY OF THE INVENTION

The purpose of the present invention is to solve the above-described problem and to provide a method by means of which a doctor treating a patient is able to monitor the health of the patient under his care more accurately and effectively than previously. This object is achieved with a method according to the invention in which a patient independently performs measurements and which is characterized by supplying the results of the measurements via a communications device utilizing a wireless data transmission link to a data processing system available to a person monitoring the patient's health, and monitoring the patient's health by means of the data stored in the data processing system.

The expression "a person monitoring the patient's health" refers in this connection to anyone who participates in the treatment of the patient and who needs to monitor the development of the patient's health. Therefore this person does not necessarily have to be a doctor, but for example in connection with treating a child the parents may monitor the patient's health.

The invention also relates to a system wherein the method according to the invention can be utilized. The system according to the invention is characterized in that the measuring device consists of a measuring unit and a communications device that utilizes a wireless data transmission link and that is connected to said unit, the measuring device comprising means for supplying the result of the measurement carried out by the measuring unit via said data transmission link to said data processing system. The aforementioned data processing system may be a data processing system of a hospital, for example, or some other corresponding support unit.

The invention further relates to a portable measuring device with which the method according to the invention can be applied. The measuring device according to the invention is characterized in that the measuring device consists of a measuring unit and a communications device that utilizes a wireless data transmission link and that is connected to said unit, the measuring unit comprising means for supplying the result of the measurement via the communications device to a data processing system available to a person treating the patient.

The term "communications device" refers in this connection to any device which is suitable for wireless communications and by means of which the patient can transmit his measurement results to the data processing system available to his doctor, regardless of where the patient is at the moment. Such a communications device may be for example any radio transmitter, such as a mobile phone operating via base stations or possibly via a satellite, or for example a two-way pager.

The invention is based on the idea that when the results of the measurements carried out by the patient himself are transmitted automatically via a wireless data transmission link directly to the person or persons treating him, the doctor is able to monitor the development of the patient's health better than before and to help the patient in his self-care, so that the treatment of the patient is considerably improved. Wireless data transmission enables the doctor to obtain the measurement results concerning the patient's health in real time, if required, regardless of the patient's current location. Therefore it is not necessary for the patient and the doctor to meet personally in order for the doctor to be informed about the latest developments in the patient's health, but the patient can transmit the latest measurement results to the doctor for example from a summer cottage situated in a remote area, whereafter the patient and the doctor may discuss further treatment for example by phone, if necessary.

Also, for example when examining the recent measurement results of the patient, the doctor may discover that the patient's medication should be changed and he can thus ask the patient to make an appointment for more detailed tests. The primary advantages of the arrangement according to the invention therefore include the accurate and rapid transmission of measurement results from the patient to the doctor, the gathering of measurement results in the patient's normal environment so that for example the patient's actual exercise level and/or diet are more apparent in the measurement results and hospital surroundings do not distort the results, and the possibility for the doctor to monitor the recent development of the patient's health without the patient having to make an appointment with the doctor, in which case the patient can visit the doctor/the hospital only when he really needs and not according to a predetermined schedule.

In a preferred embodiment of the measuring device according to the invention, the measuring device consists of a mobile phone and of a combination of a measuring unit and a battery placed in the battery space of the mobile phone. This embodiment of the invention is highly advantageous since it can be implemented utilizing prior components, i.e. for example a mobile phone of the GSM system and an existing mobile communication system, and therefore the application of the arrangement according to the invention is very economical. Also, when the measuring unit is designed in such a way that it can be placed in the battery space of the mobile phone, the number of the articles the patient has to carry with him is minimized. Therefore the patient can easily carry the measuring device with him without attracting the attention of other people in the same way as when carrying a separate measuring device. Another advantage of the mobile phone is that the doctor can contact the patient any time with the phone for example in a situation where the doctor has noticed a need for a personal contact on the basis of the patient's recent measurement results, for example when the risk of hypoglycaemia has increased.

The preferred embodiments of the method, system and measuring device according to the invention are disclosed in the appended dependent claims 2, 4 and 6 to 11.

BRIEF DESCRIPTION OF THE DRAWINGS

In the following, the invention will be described in greater detail by way of an example by means of a preferred embodiment illustrated in the accompanying figures, in which.

DESCRIPTION OF THE PREFERRED EMBODIMENTS

Figure 1:
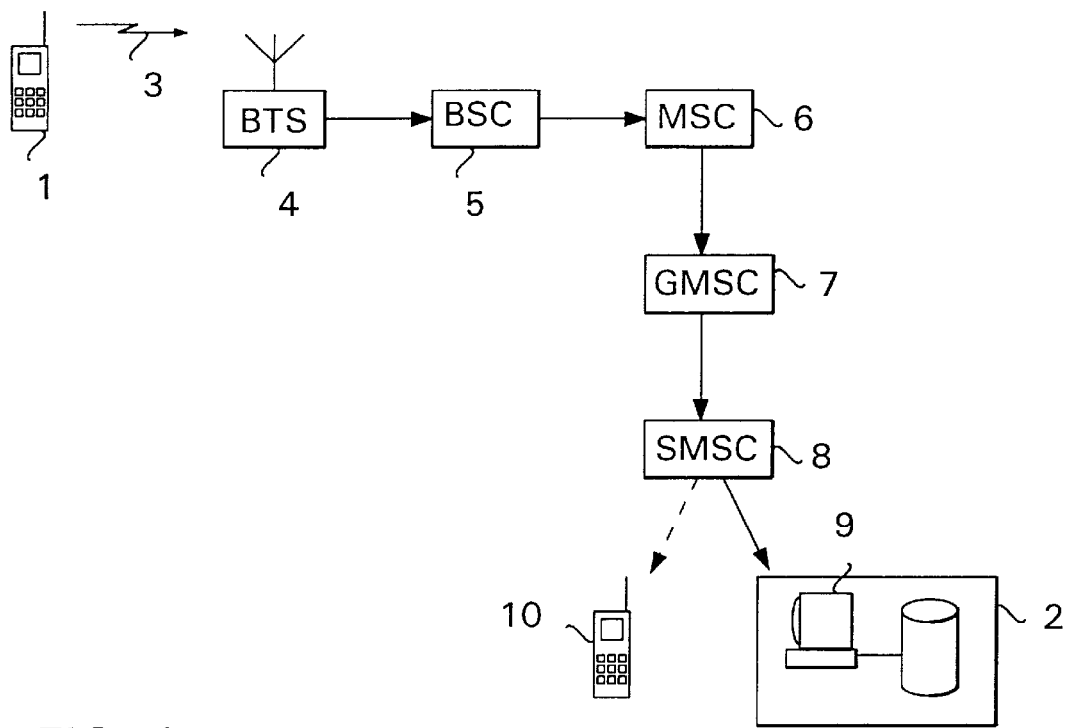
FIG. 1 illustrates the first preferred embodiment of the system according to the invention.

FIG. 1 is a block diagram of the first preferred embodiment of the system according to the invention. The measuring device 1 shown in FIG. 1 consists of a mobile phone and a measuring unit. The invention will be described below by way of an example, assuming that the measuring unit comprises means for measuring the blood glucose level, even though the measuring unit may also comprise means for performing some other measurement, such as for measuring blood pressure, fever or pulse.

When a patient has carried out a measurement utilizing the measuring unit comprised by the measuring device 1, the measuring device 1 transmits the measurement result to the data processing system 9 of the hospital 2. This takes place in such a way that the mobile phone that forms a part of the measuring device 1 and that is assumed to be, by way of an example, a mobile phone of the GSM mobile communication system (Groupe Spécial Mobile) transmits the measurement result supplied by the measuring unit in the form of a short message 3 to a base station 4. The base station 4 forwards the message via a base station controller 5, a mobile services switching centre (MSC) 6 and a gateway centre 7 to a short message service centre (SMSC) 8 in the mobile system. The GSM system and the short message service thereof are described in greater detail for example in *The GSM System for Mobile Communications* by M. Mouly and M.-B. Pautet, Palaiseau, France, 1992, ISBN: 2-9507190-0-7, and therefore they will not be described in greater detail in this connection.

The short message service centre 8 may be programmed specifically in each case to transmit the short message received from the patient's measuring device 1 directly to the data processing system 9 of the hospital 2, where it is stored in the patient database of the hospital, or alternatively the message can be temporarily buffered to the short message service centre 8, until the doctor treating the patient reads it via the data processing system 9 of the hospital 2 or alternatively for example via his mobile phone 10. Therefore the doctor treating the patient has at all times access to the patient's measurement results regardless of the current location of the doctor and/or the patient.

The hospital data processing system 9 preferably contains for each patient the results of the measurements, carried out with the patient's own measuring device 1 or alternatively performed at the hospital, for a period of several years. Therefore the doctor treating the patient can monitor the development of the patient's health via the data processing system 9 for example by utilizing a trend analysis also when the doctor and the patient have not been in direct communication with each other.

If required, the patient may also transmit information other than the measurement result and the time of measurement from his measuring device 1. Thus, for example a patient with diabetes can supply data concerning for example his diet, dosage of insulin, exercise or the like via the keyboard of the measuring device, and also this information will be forwarded by means of a short message to the data processing system 9 used by the doctor treating the patient.

The hospital data processing system 9 preferably also provides other reports concerning individual patients and/or for example all patients with a certain disease. Therefore, also users other than the patient's own doctor can utilize the data gathered in the data processing system for example for the purpose of drafting different types of statistics or instructions for treatment. Possible other users include for example authorities, insurance companies, research centres and the like.

Figure 2:
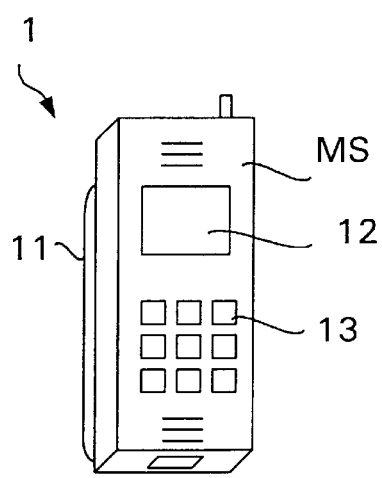
FIGS. 2 and 3 illustrate the first preferred embodiment of the measuring device according to the invention.
Figure 3:
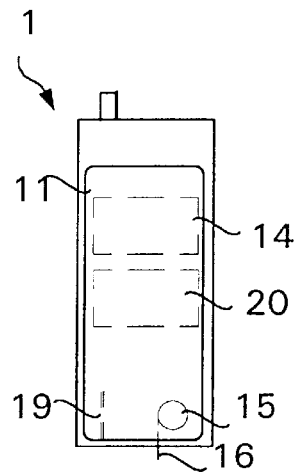

FIGS. 2 and 3 illustrate the first preferred embodiment of the measuring device according to the invention. In FIG. 2, the measuring device is shown in a diagonal front view and in FIG. 3 in a rear view. The measuring device 1 consists of a mobile phone MS and a measuring unit 11 placed in the battery space of the mobile phone. The measuring unit and the mobile phone may naturally also be entirely separate components that are connected for example by means of a cable, in which case the patient must carry with him two separate parts instead of one, however.

The mobile phone MS shown in FIGS. 2 and 3 may be for example a phone of the GSM system known per se, provided with connectors by means of which the measuring unit 11 placed in the battery space can be connected to a communication bus of the phone. The phone may also have been subjected to changes concerning its software, so that the measuring unit 11 is able to utilize the display 12 and the keyboard 13 of the phone.

The measuring unit 11 is designed in such a way that it fits in the battery space of the mobile phone MS when the normal battery of the phone has been removed therefrom. In addition to the measuring means, the measuring unit therefore also comprises a battery 14 that supplies an operating voltage to the mobile phone MS and to the measuring unit 11 itself. The measuring unit preferably further comprises a back-up battery that makes it possible to also perform measurements with the measuring unit when the battery 14 has run down and no calls can be made from the mobile phone.

FIG. 3 illustrates the measuring means provided in the measuring unit of the measuring device 1. The measuring device shown in FIG. 3 comprises means for measuring the blood glucose level in an electric manner known per se, even though the measuring device could also be provided with means for carrying out the measurement optically or even without a need to penetrate the skin.

The measuring unit 11 comprises an integrated lancet 19 that may be operated for example with a spring so that the patient can easily prick the skin with it. The patient thereafter pulls out a strip 16 that is known per se and that is placed for example on a reel 15 in the measuring unit 11, the strip being impregnated with the drop of blood (the structure of the strip is illustrated in greater detail in FIG. 4). One reel provided in the measuring unit 11 may comprise for example strips needed for one week. Electrodes which are provided in the strip and between which the drop of blood is absorbed are connected to an electronic section provided in the measuring unit 11, the section comprising means for measuring the blood glucose level. For this purpose, the electronic section 20 comprises for example an A/D converter and a memory, for example a ROM table, where the glucose levels corresponding to different electric measurement values are stored. If the measuring unit employs optical measurement instead of resistance measurement, the ROM table correspondingly stores glucose levels corresponding to different optical measurement values.

The electronic section 20 also preferably comprises a memory where the measurement result can be stored. Therefore, carrying out a measurement does not require the mobile phone MS to be connected to the measuring unit 11 at the moment of measurement, but the measuring unit can operate independently so that the measurement result is stored in the memory provided therein. Next time when the measuring unit 11 is connected to the mobile phone MS (or when the measurement is complete, if the measuring unit has been continuously connected to the mobile phone), the electronic section of the measuring unit 11 activates the short message transmission described in connection with FIG. 1 in order to forward the measurement result to the data processing system of the doctor treating the patient.

The electronic section 20 preferably comprises means for storing in memory several earlier measurement results and for compiling statistics on them, so that the patient can browse through previous measurement results and monitor their development by means of the keyboard 13 and the display 12 of the mobile phone MS. The electronic section may also store a special program related to the act of measurement, the program guiding the patient in carrying out the measurement for example by providing advice via the display 12. The program may for example provide the patient with a prompt urging him to immediately contact the doctor if the measurement results exceed or fall below a predetermined threshold value.

Figure 4:
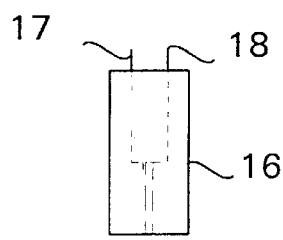
FIG. 4 illustrates the strip shown in FIG. 3.

FIG. 4 illustrates the strip 16 shown in FIG. 3. The strip 16 known per se, having for example the outer dimensions of 2 mm×7 mm, comprises two integrated electrodes 17 and 18. Between the electrodes there is a capillary which is impregnated with a blood sample. The blood sample can thereafter be subjected to electrical measurement by connecting the ends of the electrodes 17 and 18 projecting from the strip to the measuring unit.

It should be understood that the above description and the related figures are only intended to illustrate the present invention. Different variations and modifications of the invention will be evident for those skilled in the art without departing from the scope and spirit of the invention disclosed in the appended claims.

We claim:

1. A system for use in monitoring the health of a patient, the system comprising:

a portable measuring device for carrying out a measurement to provide measurement results suitable for evaluating the patient's health;

data processing system that maintains data corresponding to the measurement results;

said measuring device comprising a measuring unit and a mobile phone having a battery space and using a wireless data transmission link, the mobile phone being connected to said measuring unit, wherein the measuring unit is located in the battery space of the mobile phone and is connected to a communication bus of the mobile phone, the measuring unit comprising means for supplying the measurement results to the mobile phone via the communication bus and further via a mobile communication network to the data processing system.

2. A system according to claim 1, wherein the measuring unit comprises means for measuring the patient's blood glucose level to provide the measurement results.

3. A portable measuring device comprising:

a measuring unit for carrying out a measurement to provide measurement results suitable for evaluating a patient's health, and a mobile phone having a battery space and using a wireless data transmission links, the mobile phone being connected to said measuring unit, wherein the measuring unit is located in the battery space of the mobile phone and is connected to a communication bus of the mobile phone, the measuring unit comprising means for supplying the measurement results to the mobile phone via the communication bus and further via a mobile communication network to a data processing system.

4. A portable measuring device according to claim 3, wherein the measuring unit comprises means for measuring the patient's blood glucose level to provide the measurement results.

5. A portable measuring device according to claim 3, wherein the measuring device comprises means for measuring the patient's blood glucose level including measuring strips maintained on a reel inside the measuring device.

6. A portable measuring device according to claim 3, wherein the measuring unit comprises memory means for storing the measurement results when the measuring unit is separate from the mobile phone and means for supplying the stored measurement results via the mobile phone to the data processing system when the measuring unit is connected to the mobile phone.

7. A portable measuring device according to claim 3, wherein the mobile phone utilizes a GSM mobile system and comprises means for transmitting the measurement results in the form of a short message of the GSM system.

* * * * *

UNITED STATES PATENT AND TRADEMARK OFFICE
CERTIFICATE OF CORRECTION

PATENT NO. : 5,772,586
DATED : June 30, 1998
INVENTOR(S) : HEINONEN ET AL.

It is certified that error appears in the above-indentified patent and that said Letters Patent is hereby corrected as shown below:

Claim 1, col. 6, line 17, after "health;" insert --and--.

Claim 1, col. 6, line 18, before "data processing" insert --a--.

Claim 3, col. 6, line 39, delete "links" and insert --link--.

Signed and Sealed this

Twenty-fifth Day of August, 1998

Attest:

BRUCE LEHMAN

Attesting Officer

Commissioner of Patents and Trademarks